United States Patent [19]

McCaughan, Jr.

[11] Patent Number: 4,660,925
[45] Date of Patent: Apr. 28, 1987

[54] APPARATUS FOR PRODUCING A CYLINDRICAL PATTERN OF LIGHT AND METHOD OF MANUFACTURE

[75] Inventor: James S. McCaughan, Jr., Galena, Ohio

[73] Assignee: Laser Therapeutics, Inc., Worthington, Ohio

[21] Appl. No.: 728,689

[22] Filed: Apr. 29, 1985

[51] Int. Cl.$^4$ ............................................... G02B 6/02
[52] U.S. Cl. ........................... 350/96.15; 128/303.1; 128/397; 350/96.10; 350/96.20; 350/320; 362/32
[58] Field of Search ............... 350/96.10, 96.15, 96.20, 350/96.29, 96.30, 320; 362/32; 128/303.1, 395–398

[56] References Cited

U.S. PATENT DOCUMENTS

| | | | |
|---|---|---|---|
| 1,542,183 | 6/1925 | Steinberg | 350/96.10 X |
| 4,233,493 | 11/1980 | Nath | 350/96.10 X |
| 4,516,022 | 5/1985 | Lindgren | 350/96.10 X |

FOREIGN PATENT DOCUMENTS

| | | | |
|---|---|---|---|
| 58-07604 | 1/1983 | Japan | 350/96.15 |
| 59-29206 | 2/1984 | Japan | 350/96.10 |

OTHER PUBLICATIONS

Fujii et al., "Light Scattering Properties of a Rough-Ended Optical Fibre," *Optics and Laser Technology*, vol. 16, No. 1, Feb. 1984, pp. 40–44.

Primary Examiner—John Lee
Attorney, Agent, or Firm—George Wolken, Jr.

[57] ABSTRACT

The present invention discloses an optical radiating apparatus constructed on one end of a light-conducting optical fiber such that, upon encountering this radiator, light is caused to leave the fiber and radiate in a cylindrical pattern with respect to the central axis of the fiber. This optical radiator is constructed such that the pattern of radiated light is nearly uniform in intensity in a cylindrical pattern, without areas of light intensity significantly different from the average distribution around the circumference of the cylinder. The present invention also discloses a method to manufacture the above-described light radiating apparatus, ensuring uniformity of light intensity and the ability to transmit relatively intense light without developing regions of optical, thermal or mechanical damage, and without the need to reshape the core of the optical fiber.

4 Claims, 3 Drawing Figures

U.S. Patent  Apr. 28, 1987  4,660,925
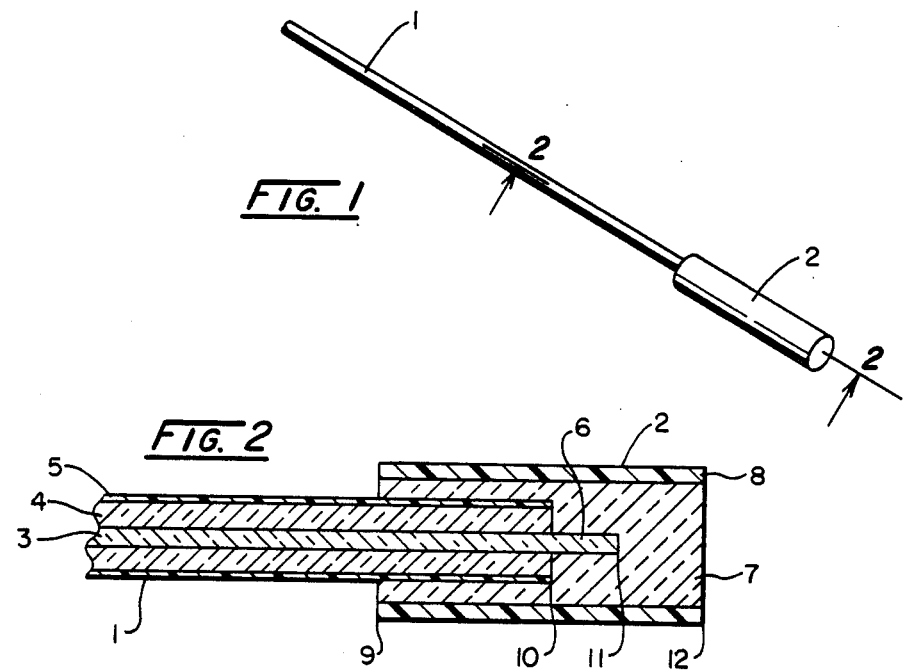
FIG. 1
FIG. 2
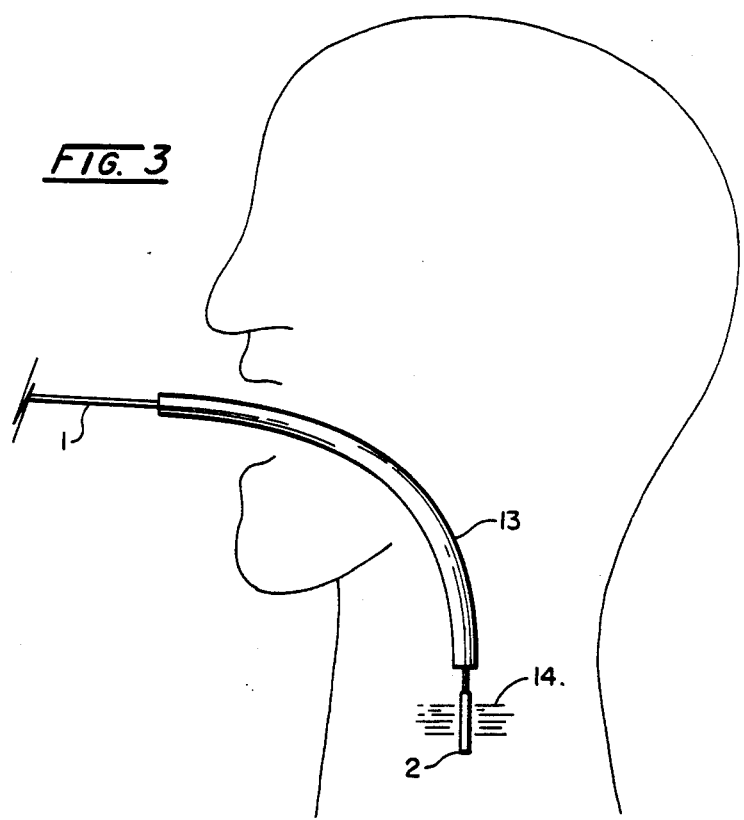
FIG. 3

APPARATUS FOR PRODUCING A CYLINDRICAL PATTERN OF LIGHT AND METHOD OF MANUFACTURE

BACKGROUND OF INVENTION

This invention relates to a fiber optic device and more particularly to a device for dispersing light propagating along an optical fiber into an approximately uniform cylindrical pattern surrounding the fiber, and a method to manufacture this device.

During the course of the last several years, a new method of treatment for cancer in humans has been receiving considerable attention. Known as "photodynamic therapy" (PDT), this treatment makes use of two well-documented effects to destro cancerous tissues. The two effects are: (1) the propensity of certain chemicals to concentrate (or to remain) preferentially in cancer cells, and (2) the ability of light with a specific wavelength to promote photochemical reactions which, in the absence of such light, would proceed extremely slowly or not at all. The first effect is the foundation of the entire field of chemotherapy in which more or less "poisonous" chemicals are introduced into the patient. It is desired that lethal doses of the chamical concentrate in the cancer cells while non-lethal doses are received by normal cells. The second effect underlies the entire field of photochemistry in which light promotes many reactions not otherwise occurring. The fields of photography, photosynthesis, vision, etc. are common examples of light causing chemical reactions to proceed.

PDT combines these two effects in the treatment of cancer. A mixture of chemicals known as "hematoporphyrin derivative" (HpD) is widely known to remain preferentially in cancer cells. As extracted from serum, HpD fluoresces when exposed to light. This has proven to be a valuable diagnostic tool for many kinds of cancer. However, it has also been observed that, when illuminated with light of a specific wavelength and in sufficient intensity, HpD undergoes a photochemical reaction and kills the cell in which it resides. The exact nature of the chemical reaction which leads to the death of the host cell is not precisely defined and is the subject of continuing research at many institutions. However, the effect of killing the host cell is well-documented and is finding increasing use as a cancer treatment in the U.S. and elsewhere.

In clinical use, a patient is injected with HpD in an appropriate dosage as determined by the attending physician. The HpD permeates cells throughout the body, but dissipates from normal cells much more rapidly than from cancer cells. Typically, 48 to 72 hours after injection, HpD will remain in the patient's cancerous cells in much greater concentrations than in the surrounding normal tissue. Thus, exposing the cancerous region during this sensitive period to suitable light (for HpD this is red light with wavelength close to 630 nanometers) of sufficient intensity (as determined by the physician considering such things as the depth of the tumor, its nature, location, orientation etc.) will lead to preferential destruction of the cancerous tissues exposed to light.

PDT has several attractive features. HpD by itself is not a "poison". Thus, unlike much conventional chemotherapy, the patient has virtually no discmforting side effects from the treatment. (However, the patient is overly sensitive to light and is advised to stay out of sun light for several weeks following treatment.) PDT does not interfere with other modes of treatment. It can be readily used as part of a whole range of treatments the physician may prescribe for the patient. Most attractive of all, PDT is the first definite example of a method of cancer treatment combining photochemistry with preferential concentration in cancer cells. Since both effects are known to be widespread, HpD will almost certainly not be the last treatment to work in this manner.

However, some problems remain with PDT. The treatment is not effective unless suitable intensity of light is brought to bear upon the tumor. Thus, for cancers that rapidly spread over great areas, rapidly invade tissues deeply, or otherwise cannot be reached with light, PDT may not be the method of choice for the physician.

The present invention concerns a device which allows the physician to effectively deliver intense light to certain tumor sites not otherwise conveniently reached. The device must be capable of carrying intense radiation without overheating and destroying itself. The device must provide a uniform pattern of illumination so the physician can irradiate the entire treatment area with intense radiation lethal to the cancer cells, without leaving "dark areas" of undestroyed cells to cause future problems for the patient.

For cancers occurring in tubular regions of the body, the appropriate pattern of radiation for treatment is a uniform cycylindrical pattern. Thus, for PDT treatment of esophogeal cancer, an optical fiber is required to be equipped with an apparatus at one tip that disperses light propagating along the fiber in a uniform cylindrical pattern. This optical radiating apparatus must produce a reasonably uniform pattern of light, so the physician can have reasonable confidence in his applied dosage level. The apparatus must also be able to transmit reasonably intense radiation for effective treatment without developing "hot spots", optical, thermal or mechanical damage. Finally, the apparatus must perform these tasks in an environment in which it encounters blood, mucus, extraneous bits of tissues, and other substances which may contaminate its optical properties. Such an optical radiating apparatus for producing a uniform cylindrical pattern of light, and a method for manufacturing such an apparatus, is the subject of the present invention.

There have been a few other approaches to the problem of producing a uniform cylindrical pattern of intense light around the tip of an optical fiber. Work reported by Fujii et. al. in *Optics and Laser Technology*, February 1984, p. 40–44, considers the scattering of light from the tip of an optical fiber which has been subjected to various chemical etching and roughening procedures. While the patterns of light are measured precisely, they are far from uniform cylindrical patterns and not very useful in practical treatments.

Another approach to producing approximately uniform cylindrical patterns of light is that taken by the Quentron Optics Pty Ltd of Adelaide, Australia in their optical fibers marketed under the trade designation "QF-IA" and "QF-IV". The Quentron fiber has a light carrying core which is tapered to a point, allowing the propogating light to escape at each point along the tapered core. It is anticipated that the need to taper the core of the optical fiber will add substantially to the cost and complexity of manufacture.

The present invention comprises a coating for the tip of an optical fiber, and method of producing the coated tip, which produces an approximately uniform cylindrical pattern of light and requires no shaping of the fiber core.

SUMMARY AND OBJECTS OF THE INVENTION

The present invention discloses an optical radiating apparatus constructed on one end of a light-conducting optical fiber such that, upon encountering this radiator, light is caused to leave the fiber and radiate in a cylindrical pattern with respect to the central axis of the fiber. This optical radiator is constructed such that the pattern of radiated light is nearly a uniform cylindrical shape. Also the light is dispersed around this cylindrical pattern in a nearly uniform intensity distribution, without areas of light intensity significantly different from the average distribution on the surface of the cylinder. The above properties are achieved without the need to reshape the cylindrical core of the optical fiber.

The present invention also discloses a method to manufacture the above-described light radiating apparatus. For the intended use in cancer treatment, significant light intensity must be carried by the optical fiber and the radiating apparatus without developing "hot spots" and burn regions, to the possible detriment of the patient. The radiating apparatus must maintain its structural integrity and uniform cylindrical pattern of radiated light in an environment of mucus, blood, tissue and other substances encountered in the treatment of a patient.

Thus, a primary object of the present invention is to provide an apparatus for producing a uniform cylindrical pattern of light at the tip of an optical fiber.

Another object of the present invention is to provide a uniform optical radiator as described, in a configuration suitable for use in patients.

Another object of the invention is to provide an optical radiator able to disperse relatively intense radiation without suffering optical, thermal or mechanical damage.

Another object of the present invention is to provide a method of manufacturing the optical radiator with the properties described in a reliable, and reproducible fashion, without the necessity of reshaping the core of the optical fiber from its usual cylindrical shape.

DESCRIPTION OF DRAWINGS

FIG. 1: A perspective view of the optical radiating apparatus on the tip of an optical fiber.

FIG. 2: Cross-sectional view of the optical radiating device as mounted on the tip of an optical fiber, viewed as a section through the central axis of the optical fiber (noted 2 in FIG. 1).

FIG. 3: Cut-away view of a patient's head with the present invention inserted into the esophagus through a flexible tube.

DESCRIPTION OF PREFERRED EMBODIMENTS

FIG. 1 shows in perspective view a typical optical fiber, 1, conducting light from the upper left portion of the figure into the region of an optical radiating apparatus, 2. This radiating apparatus surrounds one terminus of the optical fiber 1. The apparatus 2 is the subject of the present invention. It disperses light propagating along optical fiber 1 into a uniform cylindrical pattern.

Apparatus 2 is typically small enough to insert into a patient, frequently through a tube into the esophagus or bronchus, or into other regions of the body where approximately cylindrical patterns of light are required. Another property required of radiating apparatus 2 is that it withstand the relatively high intensities of light it must carry. Typically, up to about 200 milliwatts per sq. cm. of 630 nanometer radiation must be delivered to the tumor. Thus, the fiber and the optical radiating apparatus should be able to withstand up to a few watts of power without suffering significant optical, thermal or mechanical damage even when used in vivo.

FIG. 2 shows in cross-sectional view the optical fiber terminating in radiating apparatus 2. The light-carrying core of the fiber is shown as 3 in FIG. 2. The cladding region having a relatively low index of refraction with respect to the core, 3, is shown as 4. The protective sheathing, typically polyethylene or other plastic, is shown as 5. As shown in FIG. 2, the core region extends beyond the cladding and sheating, typically for a distance of approximately 1.5 to 3 millimeters. The region surrounding the exposed core, 6, is filled with light scattering material, 7. This entire structure is then surrounded by a protective tubing 8, typically polyethylene or glass. The length of the optical radiator is typically approximately 2 cm in length and 1 mm in inner diameter. However, the uniform cylindrical light scattering properties depend upon achieving the correct balance of light leaving the fiber core 6, and being scattered by the scattering region 7. Thus, there is no well-defined set of lengths for the various regions, but ratios are more important. For other purposes, optical radiators of much greater length can be fabricated by analogous methods to those disclosed here. The distance from the upper end of the radiating apparatus, 9, to the termination of the cladding and sheathing, 10, is typically twice as long as the distance from 10 to the termination of the core, 11, which is approximately equal to the distance to the lower terminus, 12, of the radiating apparatus. The region of scattering material from 9 to 10 in FIG. 2 lies upstream from the exposed, light-carrying core, 11. Thus, this region is not primarily contributing to the light scattering properties of the apparatus, but serves to provide better binding of the scattering material, 7, to the optical fiber, 1. The primary light dissipating portion of region 7 lies in the region from 10 to 12 in FIG. 2.

In order to achieve a uniform cylindrical pattern of light around the circumference of the cylinder, it is necessary that the scattering power of the scatterer 7 increase along the length of the scattering region from 10 to 12 in FIG. 2. The amount of light dispersed away from the central optical axis of the core is proportional to the incident light intensity. The constant of proportionality is referred to as the "scattering power." As light is lost from the incident propagating beam into the outer portions of the cylinder, less incident light is available "downstream". Thus, to maintain a constant scattered light intensity, the scattering power must increase in region 7 as one scans from edge 10 to edge 12. To make a truly uniform cylindrical pattern, the scattering power must increase logarithmically.

FIG. 3 illustrates how the present invention would be used in treatment of cancer of the esophagous. The optical fiber 1 is typically passed through a flexible tube, 13, such that the optical radiating apparatus 2 is in the region of the tumor. Laser light is introduced into the end of the fiber opposite apparatus 2 at a location remote from the patient. Light is then radiated into the desired cylindrical pattern, 14, to effect the treatment.

It is critical to the proper functioning of the apparatus that the optical scattering region be free of air bubbles or other impurities which would tend to cause preferential absorption of the light and, hence, damage to the material. Another critical aspect is the method of coating the optical scattering material, 7, around the tip of the fiber to achieve a resonably uniform cylindrical pattern of scattered light. Without a uniform pattern of light, the physician cannot reliably provide the proper dosages to the entire treated area. Thus, another part of the present invention concerns the method of manufacturing this optical radiating apparatus.

A standard optical fiber suitable for transmitting red light (630 nm) is stripped by usual stripping methods exposing at one end thereof a length of core well in excess of the required 1.5 mm to 3 mm. The exposed length of core is carefully cleaved to the desired length of approximately 1.5 to 3 mm. The tip of the cleaved core is polished flat using, typically, cerium oxide polishing compound although polishing directly with a suitable polishing cloth may also be used.

Having an optical fiber with a short length of exposed, polished core, the scattering region is constructed to produce the desired uniform cylindrical scattering pattern. A typical scattering medium, which gives preferred performance in this invention, is composed of approximately equal parts powdered quartz (crystobolite) and an optical adhesive. Any of several optical adhesives manufactured by the Norland Company have been tested and found to give good performance.

A critical aspect of the manufacturing process is to apply the scattering medium such that increasing scattering is produced towards the termination of the optical radiator. One useful way to accomplish this is to propagate visible light down the optical fiber during the fabrication process. This light is typically red laser light from a HeNe laser, launched into fiber from the opposite end from that upon which the optical radiator is being constructed. This light must have suitable intensity to be easily visible to the technician carrying out the fabrication procedure.

Using this test illumination, the technician applies (typically by dipping) the tip of the fiber into the scattering medium. The polished tip of the core region is cleaned of scattering medium upon removal from the dipping vessel. It is important in the fabrication procedure that the polished tip of the core remain free of scattering medium until the final fabrication step.

The applied scattering medium is inspected visually by the technician for bright spots or other non-uniformities in the scattering pattern from the test light. Any such imperfections are manually smoothed by the technician before curing. The scattering medium, typically being a mixture of curable optical adhesive and quartz powder, is then cured by exposure to ultraviolet light from a standard source, typically as recommended by the adhesive manufacturer. Further layers of scattering medium are applied, inspected, smoothed and cured as described above until the desired light scattering pattern is obtained.

The final manufacturing step involves inserting the fiber, with its coatings of scattering medium, into a tube, typically plastic (such as polyethylene) or glass. The spaces remaining in the interior of the tubing are carefully filled with scattering medium. This is typically accomplished by inserting, via hypodermic syringe, a small amount of scattering medium into the tubing before the optical fiber and radiating assembly are inserted into the tubing. Care must be exercised to leave no air bubbles or other foreign substances that can cause "hot spots" or otherwise lead to optical, thermal or mechanical damage. The final curing is performed, the tubing is cut to the desired length, and the fiber with its appended optical radiating apparatus is ready for use. We note in passing that the tubing 8 in FIG. 2 is shown co-terminus with the scattering medium 7. This is not critical to the practice of the present invention, but it is frequently advantageous in practice (to facilitate insertion through a bronchoscope, for example) to leave excess tubing 8, cut at an angle other than perpendicular to the optical fiber axis, 2 in FIG. 1, to act as the leading edge in inserting the device into the proper area for treatment. Such minor modifications are standard techniques well known in the art.

What is claimed is:

1. A process for manufacturing an apparatus for radiating light in an approximately uniform cylindrical pattern comprising the steps of:
   (a) from an optical fiber comprising a central core region surrounded radially by a cladding region of lower refractive index than said core, both said cladding and core regions surrounded radially by a region of protective sheathing, removing said cladding and sheathing from a region at one end of said optical fiber, exposing said core region;
   (b) polishing the exposed terminus of said core of said optical fiber exposed by said removal of said cladding and sheathing, making a reasonably smooth, flat surface thereon;
   (c) coating said exposed core, and said cladding and sheathing adjacent thereto, with a light-scattering medium, said medium having increasing optical scattering power in a first direction parallel to the central axis of said exposed core extending from said adjacent cladding towards said poslished terminus, and uniform scattering power circumferentially around the circumference of said exposed core;
   (d) tightly inserting said light-scattering medium into a tubing, forming the outer coating of said light-scattering medium;
   (e) uniformly filling the interstices between said light-scattering medium and said tubing, excluding all entrapped air and foreign matter.

2. A process as in claim 1 wherein said lightscattering medium comprises an approximately equal mixture of powdered quartz and an optical adhesive curable by exposure to ultraviolet radiation.

3. A process as in claim 2 wherein said coating step comprises the sub-steps of:
   (i) launching laser light into said optical fiber at the end opposite that end being coated, said light of sufficient intensity to produce visible rays emanating from the region being coated;
   (ii) coating the circumference of said exposed core region with said mixture in an approximately logarithmically increasing light scattering density as determined by an observed uniform intensity in said laser light in a cylindrical pattern surrounding said core;
   (iii) curing said applied coating by exposure to ultraviolet radiation;

(iv) applying a plurality of additional layers of said light-scattering mixture by repeating sub-steps (ii) and (iii) immediately preceding.

4. A process as in claim 2 wherein said step of uniformly filling interstices between said light-scattering medium and said tubing comprises the sub-steps of:

(i) placing a second quantity of said light-scattering medium in an uncured condition into said tubing;
(ii) inserting said coated optical fiber into said tubing, thereby forcing out entrapped air and foreign substances;
(iii) curing said second quantity of light-scattering medium.

* * * * *